United States Patent [19]

Forte et al.

[11] Patent Number: 5,689,033
[45] Date of Patent: *Nov. 18, 1997

[54] PROCESS FOR REMOVAL OF IMPURITIES FROM LIGHT PARAFFIN ISOMERIZATION FEEDSTOCKS

[75] Inventors: Paulino Forte, Yonkers, N.Y.; Stanley J. Frey, Palatine, Ill.

[73] Assignee: UOP, Des Plaines, Ill.

[*] Notice: The term of this patent shall not extend beyond the expiration date of Pat. No. 5,582,714.

[21] Appl. No.: 642,092

[22] Filed: May 2, 1996

Related U.S. Application Data

[62] Division of Ser. No. 406,441, Mar. 20, 1995, Pat. No. 5,569,788.

[51] Int. Cl.$^6$ ..................................................... C07C 7/10
[52] U.S. Cl. ............... 585/833; 208/208 R; 208/236; 208/237; 208/240; 208/255; 208/242; 585/864; 585/857
[58] Field of Search ................. 208/208 R, 236, 208/237, 240, 255, 242; 585/833, 864, 857

[56] References Cited

U.S. PATENT DOCUMENTS

| | | | |
|---|---|---|---|
| 2,720,547 | 10/1955 | Wolff et al. | 260/614 |
| 3,726,942 | 4/1973 | Louder | 260/683.61 |
| 4,081,354 | 3/1978 | Christman | 208/235 |
| 4,118,425 | 10/1978 | Herbstman | 260/614 A |
| 4,204,077 | 5/1980 | Woods et al. | 568/697 |
| 4,218,569 | 8/1980 | Chase et al. | 568/697 |
| 4,219,678 | 8/1980 | Obenaus et al. | 568/697 |
| 4,252,541 | 2/1981 | Herbstman | 44/56 |
| 4,329,516 | 5/1982 | Al-Muddarris | 568/697 |
| 4,447,653 | 5/1984 | Vora | 568/697 |
| 4,556,461 | 12/1985 | Ogura et al. | 203/29 |
| 4,558,168 | 12/1985 | Gussow et al. | 585/324 |
| 4,626,341 | 12/1986 | Verachtert | 208/235 |
| 4,686,317 | 8/1987 | Quann et al. | 585/860 |
| 4,754,078 | 6/1988 | Vora et al. | 568/697 |
| 4,816,607 | 3/1989 | Vora et al. | 568/697 |

(List continued on next page.)

OTHER PUBLICATIONS

Stinson, Stephen C., "New Plants Processes Set for Octane Booster," *Chemical and Engineering News*, Jun. 25, 1979, pp. 35–36.

Obernaus et al., "Huels–Process: Methyl Tertiary Butylether." paper presented at The American Institute of Chemical Engineers, 85th National Meeting, Jun. 4–8, 1978.

"Modern Petroleum Technology," Edited by Hobson et al., pp. 334, 1973.

*Primary Examiner*—Glenn A. Caldarola
*Assistant Examiner*—Nadine Preisch
*Attorney, Agent, or Firm*—Thomas K. McBride; John G. Tolomei; Richard P. Silverman

[57] ABSTRACT

A process is directed to the removal of impurities such as sulfur compounds, oxygenates, and/or olefins from a light paraffin hydrocarbon feedstock such as a $C_4$–$C_6$ fraction, which may be used subsequently in an isomerization process in an integrated complex for the production of ethers such as MTBE and TAME. The hydrocarbon feedstream is passed to a removal zone wherein the hydrocarbon feedstream is contacted with a selective solvent for the removal of the impurities comprising at least one of sulfur compounds, oxygenates and olefins to provide a rich solvent stream and a treated hydrocarbon stream. The rich solvent comprising the trace impurities is contacted with a stripping medium stream to regenerate the selective solvent in a stripping zone. The removal zone may be a liquid-liquid extraction zone or a gas absorption zone. The selective solvent comprises a water miscible organic liquid having a low molecular weight preferably less than about 400 and more preferably having a molecular weight of less than about 200. The process is particularly useful in removing impurities such as sulfur, oxygenates and/or olefins which are harmful to the isomerization catalyst. The process replaces separate olefins, oxygenate, and sulfur removal processes resulting in simplified processing schemes.

13 Claims, 3 Drawing Sheets

U.S. PATENT DOCUMENTS

| | | | |
|---|---|---|---|
| 4,906,788 | 3/1990 | Scott et al. | 568/697 |
| 5,085,740 | 2/1992 | Lee et al. | 203/51 |
| 5,122,236 | 6/1992 | Smith, Jr. et al. | 203/43 |
| 5,237,115 | 8/1993 | Makovec et al. | 585/314 |
| 5,260,493 | 11/1993 | Harandi et al. | 568/697 |
| 5,569,788 | 10/1996 | Forte et al. | 568/697 |
| 5,582,714 | 12/1996 | Forte | 208/237 |

PROCESS FOR REMOVAL OF IMPURITIES FROM LIGHT PARAFFIN ISOMERIZATION FEEDSTOCKS

This is a divisional of application Ser. No. 08/406,441 filed on Mar. 20, 1995 now U.S. Pat. No. 5,569,788.

FIELD OF THE INVENTION

This invention is specifically related to the removal of impurities from light paraffin streams.

DISCUSSION OF RELATED ART

Etherification processes are currently in great demand for making high octane compounds which are used as blending components in lead-free gasoline. These etherification processes will usually produce ethers by combination of an isoolefin with a monohydroxyl alcohol such as methanol or ethanol. The etherification process can also be used as a means to produce pure isoolefins by cracking of the product ether. For instance, pure isobutylene can be obtained for the manufacture of polyisobutylenes and tert-butyl-phenol by cracking methyl tertiary butyl ether (MTBE). The production of MTBE has emerged as a predominant etherification process which uses $C_4$ isoolefins as the feedstock. A detailed description of processes, including catalyst, processing conditions, and product recovery, for the production of MTBE from isobutylene and methanol are provided in U.S. Pat. Nos. 2,120,547 and 4,219,678 and in an article at page 35 of the Jun. 25, 1979 edition of Chemical and Engineering News. The preferred process is described in a paper presented at The American Institute of Chemical Engineers, 85th National Meeting on Jun. 4-8, 1978, by F. Obenaus et al. The above references are herein incorporated by reference. Other etherification processes of current interest are the production of tertiary amyl methyl ether (TAME) by reacting $C_5$ isoolefins with methanol, and the production of ethyl tertiary butyl ether (ETBE) by reacting $C_4$ isoolefins with ethanol, the production of tertiary amyl ethyl ether (TAEE) by reacting $C_5$ isoolefins with ethanol, and the production of tertiary hexyl methyl ether (THME) by reacting $C_6$ isoolefins with methanol.

Typical process arrangements include an isomerization step ahead of and isolated from dehydrogenation and further processing steps. Since the isomerization of relatively short chain paraffins yields a fixed ratio of isoparaffin to paraffin, it is advantageous to recycle unconverted paraffins back to the isomerization reactor. Recycling of unconverted normal paraffins has usually been performed by separating the normal paraffins from the effluent of the isomerization reactor. Descriptions of integrated processes, including those which utilize butane isomerization and/or butane dehydrogenation, are found in U.S. Pat. Nos. 3,726,942, 4,118,425, 4,252,541 and 4,329,516.

The feed to the isomerization process must consist essentially of normal paraffins and isoparaffins. This makes the process adaptable only to such feeds or requires additional processing facilities to remove other components including sulfur compounds, olefins, and oxygenates. In addition, process streams containing unbranched paraffins that originate downstream of the isomerization zone cannot be recycled to the isomerization zone without first having these non-paraffinic components removed. These removal steps add cost and complexity to the overall etherification process by requiring processing facilities to treat both the feedstream and the recycle stream.

U.S. Pat. No. 4,816,607 to Vora is hereby incorporated by reference and discloses an integrated multistep process for the production of methyl tertiary butyl ether and other ethers from precursor light paraffins, olefins and alcohols. In simplest form a feedstream enters a fractionation column along with a recycle stream from an etherification zone. The column supplies an overhead stream containing primarily isoparaffins which enter a dehydrogenation zone which provides isoolefin to the etherification zone. In the etherification zone an alcohol reacts with the isoolefins to form an effluent comprising an ether. After removal of the ether from the effluent, the effluent comprising unreacted hydrocarbons and olefins is hydrogenated to saturate olefins and is returned as the recycle stream to the fractionation column. Normal paraffins removed from the fractionation column are passed to an isomerization zone to produce isoparaffins which are returned to the fractionation column. The isoparaffins are withdrawn in the overhead stream. Separate treatment of the feedstream is required prior to introduction to the fractionation column for the removal of sulfur compounds and other non-paraffinic components.

Paraffinic feedstreams to isomerization zones generally comprise $C_4$–$C_6$ hydrocarbons and may contain trace impurities such as sulfur compounds, oxygenates, and olefins. The sulfur compounds are generally light mercaptans such as methyl, ethyl, propyl mercaptans, and sulfides. The oxygenates may include alcohols, ethers, aldehydes, ketones, and mixtures thereof. The olefins are generally mono- and di-olefins. Water is often present and must be removed. If these impurities are not removed from the feedstream, these impurities will build up in the isomerization reactor, reducing the life of the catalyst. Commercially available techniques for removing these impurities include a combination of mercaptan removal processes such as the process described in U.S. Pat. No. 4,081,354 and 4,626,341 in combination with a dryer containing molecular sieves or a similar sorbent to remove water. The combination of the mercaptan removal process and the dryer provide an effective means for removing sulfur, but does not provide a means for removing oxygenates and olefins from the hydrocarbon stream.

Solvent extraction processes have been employed to remove oxygenates from hydrocarbon streams. U.S. Pat. No. 4,218,569 discloses a process for the removal of unreacted methanol from the unconverted hydrocarbon phase of an etherification reactor effluent by absorption or extraction with a glycol such as ethylene glycol, prior to further processing in which the methanol is detrimental as in an alkylation process. U.S. Pat. No. 4,686,317 discloses a process for removing oxygenated impurities from a hydrocarbon stream which includes extracting the oxygenates by a heavy organic polar solvent, water scrubbing the extracted hydrocarbons to recover the dissolved solvent, and combining the solvent phase from the extraction and the water phase from the scrubber and distilling to recover the solvent.

Processes are sought which remove trace impurities such as sulfur compounds, oxygenates and olefins from a hydrocarbon feedstream to an isomerization zone in an efficient manner without creating the requirement for additional process steps.

SUMMARY OF THE INVENTION

It is a broad object of this invention to provide an effective means for improving catalyst life, enhancing yields and improving the economic benefits of producing motor gasoline components in etherification units. Often the feedstream to the etherification unit can contain impurities, specifically, olefins, sulfur compounds, and oxygenates. The oxygenates may comprise alcohols, aldehydes, ketones, and mixtures thereof. The sulfur compounds may include mercaptans such as methyl, ethyl, propyl mercaptans, and mixtures thereof. The invention provides a simple and highly effective means for removal of impurities at critical points in the complex and provides an etherification complex with greater feedstock flexibility in being able to process less costly, contaminated feedstocks. In an etherification complex which contains a catalytic isomerization unit, olefins must be removed from a feedstream to the isomerization unit to avoid damaging the isomerization catalyst. By the process of the present invention, a liquid-liquid extraction or a gas absorption step is employed in a removal zone prior to an isomerization unit to remove the impurities from the feedstream. The removal zone may operate at a capacity and efficiency necessary to remove essentially all of the sulfur compound impurities, as well as olefins and oxygenates in process arrangements which eliminate traditional treating steps. The present invention provides both a means for removing olefins in the fresh feed to such an etherification complex and a means for removing unreacted olefins from an etherification reactor effluent thereby simplifying the complex. The invention may be employed in process arrangements that convert the $C_4$–$C_6$ product fraction from a fluid catalytic cracking process (FCC) into alkylate, or into ethers to produce high octane motor gasoline blending components for reformulated gasolines.

In one embodiment the invention relates to a process for the removal of trace impurities comprising at least one of sulfur compounds, oxygenates, and olefins from a $C_4$–$C_6$ hydrocarbon feedstream comprising the impurities. The feedstream is passed to a removal zone and therein contacted with a lean selective solvent. The lean selective solvent is selected from the group consisting of diethylene glycol, triethylene glycol, tetraethylene glycol, pentaethylene glycol, 1,3 butane glycol, 1,2 butane glycol, 1,5 pentane glycol, sulfolane, furfural, n-formyl morpholine, n-methyl-2 pyrrolidone, water, and mixtures thereof. The removal zone provides a treated feedstream depleted in the impurities and a rich-solvent stream. The rich-solvent stream is passed to a stripping zone and therein contacted with a stripping medium to provide an extract stream enriched in the impurities relative to the feedstream and a regenerated selective solvent stream. At least a portion of the regenerated selective solvent stream is returned to the removal zone as the lean selective solvent. The removal zone may be either a liquid extraction zone processing a liquid-liquid feedstream or an absorption zone processing a vapor feedstream.

In another embodiment, the invention provides a process for the removal of impurities including at least one of sulfur compounds, oxygenates, and olefins from a liquid feedstream comprising $C_4$–$C_6$ hydrocarbons and the impurities. The process comprises passing the liquid feedstream and a reflux stream at extraction conditions including an extraction temperature and extraction pressure to an extraction zone. In the extraction zone, the feedstream and the reflux stream are contacted with a selective solvent stream to provide a treated feedstream depleted in the trace impurities and a rich solvent stream. The rich solvent stream is enriched in the impurities relative to the selective solvent stream. At least a portion of the rich-solvent stream at solvent regeneration conditions including a regeneration temperature and a regeneration pressure is passed to a stripping zone. In the stripping zone, the rich-solvent stream is contacted with a stripping medium stream to provide the reflux stream, an extract stream, and a lean-solvent stream. At least a portion of the lean-solvent stream is passed to the extraction zone to provide the selective solvent stream for the extraction zone.

In a further embodiment, the invention provides a process for the removal of impurities including at least one of sulfur compounds, oxygenates, and olefins from a vapor feedstream comprising $C_4$–$C_6$ hydrocarbons and the impurities. The process comprises passing the vapor feedstream at absorption conditions including an absorption temperature and absorption pressure to an absorption zone. In the absorption zone, the vapor feedstream is contacted with a selective solvent stream to provide a treated feedstream depleted in the impurities and a rich solvent stream. The rich solvent stream is enriched in the impurities relative to the selective solvent stream. At least a portion of the rich-solvent stream at solvent regeneration conditions including a regeneration temperature and a regeneration pressure is passed to a stripping zone. In the stripping zone, the rich-solvent stream is contacted with a stripping medium stream to provide an extract stream and a lean-solvent stream. At least a portion of the lean-solvent stream is passed to the absorption zone to provide the selective solvent stream for the absorption zone.

In a still further embodiment, the invention is an etherification process for the production of an ether product from a liquid feedstream. The liquid feedstream comprises a mixture of $C_4$–$C_6$ hydrocarbons and impurities including at least one of sulfur compounds, oxygenates, and olefins. The etherification process comprises a number of steps. The feedstream is passed to an extraction zone. In the extraction zone the liquid feedstream is contacted with a selective solvent stream and a reflux stream to provide a treated feedstream depleted in the impurities and a rich-solvent stream, enriched in the trace impurities relative to the selective solvent stream. At least a portion of the rich-solvent stream is passed to a stripping zone. In the stripping zone column, the rich-solvent stream is contacted with a stripping medium stream to provide a light hydrocarbon stream, an extract stream, and a lean-solvent stream. At least a portion of the lean-solvent stream is returned to the extraction zone as the selective solvent stream. At least a portion of the light hydrocarbon stream is passed to the extraction zone as the reflux stream. The treated feedstream and a paraffin recycle stream are passed to an isomerization zone to produce an isomerized stream comprising isomerized $C_4$–$C_6$ paraffins. The isomerized stream is passed to a dehydrogenation zone to produce an isoolefin stream and the isoolefin stream is passed to an etherification zone wherein the isoolefin stream is reacted with an alcohol to produce a reactor effluent comprising an ether. The reactor effluent is passed to a separation zone to provide the ether product and an unreacted hydrocarbon stream comprising olefins. The unreacted hydrocarbon stream is passed to a complete saturation zone wherein the olefins in the unreacted hydrocarbon stream are saturated to provide a saturated hydrocarbon stream. At least a portion of the saturated hydrocarbon stream is returned to the isomerization zone to provide the paraffin recycle stream. At least a portion of the extract stream is passed to the etherification zone.

In a yet further embodiment, the invention is a process for the production of an ether product from a feedstream comprising $C_4$–$C_6$ hydrocarbons in a mixture thereof with impurities. The trace impurities include at least one of sulfur compounds, oxygenates, and olefins. The feedstream is admixed with a recycle stream comprising unreacted $C_4$–$C_6$ hydrocarbons to provide a feed admixture. The feed admixture is passed to an extraction zone employing a selective solvent to provide a treated feedstream depleted in the trice impurities and an extract stream comprising the trace impurities. The treated feedstream is passed to an isomerization zone to provide an isomerized stream comprising isomerized $C_4$-$C_6$ paraffin hydrocarbons. The isomerized stream is passed to a dehydrogenation zone to provide a dehydrogenation effluent. The dehydrogenation effluent is admixed with at least a portion of the extract stream to provide an etherification feedstream and the etherification feedstream is passed to an etherification zone. In the etherification zone, the etherification feedstream is reacted with an alcohol to produce a reactor effluent comprising an ether. The reactor effluent is passed to a separation zone to provide the ether product and an unreacted hydrocarbon stream. At least a portion of the unreacted hydrocarbon stream is passed to be admixed with the feedstream as the recycle stream.

Additional embodiments, aspects and details of this invention are set forth in the following detailed description.

DETAILED DESCRIPTION OF THE INVENTION

The hydrocarbon feedstream being treated in accordance with this invention may be derived from field butanes and light hydrocarbons from fluid catalytic cracking (FCC) units. The field butanes are typically composed of hydrocarbons having from 4 to 6 carbon atoms and are composed of paraffins and a proportion of monoolefins. The monoolefin proportion of the field butanes is typically less than 0.1 mol %, and preferably, the field butanes comprise less than 500 ppm wt monoolefins. The light hydrocarbons from FCC units typically contain from 30 to 60 mol % olefins. The paraffins include isobutane, isopentane, normal pentane, as well as propane and n-butane. The monoolefins include butene-1, butene-2, isobutene, 2-methyl-2-butene, 2-methyl-1-butene, 3-methyl-1-butene, 1-pentene, 2-pentene, cyclopentene and propylene. The hydrocarbon feedstream may also contain diolefins such as 1,3-butadiene and 1,3-pentadiene. Minor proportions of both paraffinic and olefinic molecules of various numbers of carbon atoms which can result from distillation procedures to obtain the $C_4$-$C_6$ hydrocarbons are not harmful to the process and can be present.

The hydrocarbon feedstream may contain sulfur compounds such as mercaptan sulfur. Typically, the mercaptan sulfur will include methyl mercaptan, ethyl mercaptan, propyl mercaptan, butyl mercaptan, higher mercaptans, and mixtures thereof; and the concentration of mercaptan sulfur compounds in the hydrocarbon feedstream will range from about 1 to about 5000 ppm wt.

Water and its precursors may also be present in the hydrocarbon feedstream in amounts from 5 ppm-wt to saturation which typically is about 500 ppm-wt, measured as $H_2O$. The contaminants may also include oxygenated hydrocarbon compounds, otherwise known as oxygenates, such as alcohols, ethers, aldehydes, ketones, and acids. Specific examples of these oxygenates are ethanol, methanol, isopropanol, tertiary butyl alcohol, dimethyl ether, methyl tertiary butyl ether, acetone, and acetic acid. Acetone may be present in trace amounts ranging from about 1 to about 500 wt. ppm. The feedstream may or may not have been subject to a selective hydrogenation process for the saturation of diolefins prior to its use in the pretreating process of the instant invention. Typically, the feedstream from the FCC may contain from about 1000 ppm-wt. to about 5 vol. % olefins which includes linear and branched monoolefins and diolefins such as butadiene. The effluent from a selective hydrogenation process will typically contain less than 50 ppm-wt. diolefins.

The selective solvent of the present invention selectively removes sulfur compounds such as mercaptans, sulfides, thiophenes, and mixtures thereof from a hydrocarbon stream having 4 to 6 carbon atoms per molecule. The removal zone may operate at a capacity and efficiency necessary to remove essentially all of the sulfur compound impurities, as well as olefins and oxygenates in novel process arrangements which eliminate traditional treating steps. The selective solvents employed in the instant invention, in general, are water-miscible organic liquids at the operating temperature of the process. Furthermore, the selective solvents must have a boiling point and decomposition temperature higher than the operating temperature of the process, where the operating temperature of the process refers to the liquid-liquid extraction temperature or the gas absorption temperature at which the feedstock is contacted with the solvent. The term "water-miscible" describes those solvents which are completely miscible with water over a wide range of temperatures and which have a high partial miscibility with water at room temperature, and are completely miscible at operating temperatures. By the term "essentially all of the sulfur compounds," it is meant that the sulfur content of the treated stream is preferably less than 20 ppm-wt sulfur and more preferably that it is less than 10 ppm-wt, and most preferably that it is less than 1 ppm-wt. Preferably, the oxygenate content of the treated product stream is less than 1000 ppm-mole, and more preferably, the oxygenate content ranges between 100 and 1000 ppm-mol. Preferably, the olefin content of the treated product stream is similarly reduced such that the olefin content is less than 1000 ppm-mole, and more preferably, the olefin content ranges between 100 and 1000 ppm-mole. Generally, the treated product of the present invention will be dried prior to passing the treated product to an isomerization zone or other water sensitive process.

The selective solvents employed in the instant invention are low molecular weight, preferably having a molecular weight less than about 400 and more preferably having a molecular weight less than about 200. Examples of such solvents include polyalkylene glycols of the formula:

wherein n is an integer from 1 to 5 and is preferably the integer 1 or 2; m is an integer having a value of 1 or greater, preferably between about 1 to about 20 and most preferably between about 1 and about 8; and wherein $R_1$, $R_2$ and $R_3$ may be hydrogen, alkyl, aryl, aralkyl or alkylaryl and are preferably hydrogen and alkyl having between 1 and about 10 carbon atoms and most preferably are hydrogen. Examples of the polyalkylene glycol solvents employable herein are diethylene glycol, triethylene glycol, tetraethylene glycol, pentaethylene glycol, 1,3-butane glycol, 1,2-butane glycol, 1,5-pentane glycol, water, and mixtures thereof and the like. In addition to the polyalkylene glycol solvents, the solvent may be selected from the group consisting of sulfolane, furfural, n-formyl morpholine, n-methyl-2-pyrrolidone. Preferred solvents are diethylene glycol, triethylene glycol, tetraethylene glycol, pentaethylene glycol, water, and mixtures thereof, with tetraethylene glycol being most preferred. In addition, such solvents may be combined with a cosolvent component having a low molecular weight, preferably less than 400 and more preferably having a molecular weight less than about 200. Examples of such cosolvents include a glycol ether of the formula:

$$R_4O-[CHR_5-(CHR_6-)_x-O]_y-R_7$$

wherein $R_4$, $R_5$, $R_6$ and $R_7$ may be hydrogen alkyl, aryl, aralkyl, alkylaryl and mixtures thereof with the proviso that $R_4$ or $R_7$ are not both hydrogen. The value of x is an integer from 1 to 5 preferably 1 or 2 and y may be an integer from 1 to 10 and is preferably from 2 to 8, and most preferably from 2 to 5 $R_4$, $R_5$, $R_6$ and $R_7$ are preferably selected from the group consisting of hydrogen and alkyl having 1 to about 10 carbons with the proviso that $R_4$ and $R_7$ may not both be hydrogen and most preferably $R_4$ is alkyl having from 1 to 5 carbons and $R_5$, $R_6$ and $R_7$ are hydrogen.

The isomerization contains a catalyst which is sensitive to the impurities such as sulfur, oxygenates and olefins which may be present in the hydrocarbon feedstream. For example, water poisons the preferred catalyst for the isomerization zone, therefore, a drying zone, placed ahead of the isomerization zone, removes free moisture from the hydrocarbons. The drying zone is of ordinary design such as is usually found in front of isomerization units. Two parallel chambers filled with molecular sieves are normally used so that one is on stream while the other is being regenerated. The drying zone may consist of suitable adsorbent section for water removal. By the use of the extraction or absorption process of the present invention, at least a portion of any water present in the hydrocarbon feedstream will be reduced, thus, reducing the required amount of adsorbent in the drying zone.

The isomerization zone comprises a reactor and auxiliary process equipment such as heaters, condensers, separator vessels, etc. The isomerization zone also contains a stripping column which eliminates light ends (hydrogen, methane, ethane) from the net effluent of the isomerization zone. With the preferred catalyst, this stripping column will also remove volatile chloride compounds from the isomerization zone effluent. The core of the operation of this zone is passage of a saturated hydrocarbon stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 5.0, but space velocities in the broad range of 0.5 to 12.0 can be employed if desired. The effluent of the isomerization reactor is normally separated into a hydrogen-rich recycle gas which is returned to the reactor and an isomerate-containing liquid stream which is passed into a deisobutanizer column. This liquid stream may be fractionated within the isomerization zone to allow the recycling of normal butanes and the achievement of higher conversion rates, but this is not preferred. The net hydrocarbon effluent of the isomerization zone is a mixture of isobutane and normal butane. This stream should contain at least 50 mole percent isobutane. Preferably, this stream comprises 55 to 65 mole percent isobutane.

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity. The preferred platinum group components are platinum and palladium or a mixture of platinum and palladium, with platinum being preferred. A particularly preferred method for the production of an isomerization catalyst is presented in U.S. Pat. No. 2,999,074. Other recently developed isomerization catalysts including those of a bimetallic or trimetallic nature may be used in the process. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component. A highly preferred catalyst for the isomerization zone comprises a platinum metal in a concentration of 0.05 to 1.0 wt %, an alumina support which has a chloride content of 0.001 to 5.0 wt %.

The effluent from the isomerization zone is passed to a dehydrogenation zone for the conversion of $C_4$-$C_6$ isoparaffins to $C_4$-$C_6$ olefins. The dehydrogenation zone employed in the process will contain a reaction zone and associated auxiliary process equipment such as condensers and a vapor-liquid separator which receives the partially condensed reactor effluent stream. A hydrogen-rich gas stream is preferably separated from the liquid condensed from the reactor effluent. A portion of this gas will normally be recycled and the remainder will be drawn off as a net hydrogen product gas stream. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887; 3,856,662; and 3,978,150.

The liquid stream withdrawn from the vapor-liquid separator is the effluent stream of the dehydrogenation reaction zone. This stream is passed into a fractionation system which preferably contains a single fractionation column referred to herein as the light ends stripping column. For MTBE production, this column is designed and operated to eliminate all ethane and lighter boiling components from the net dehydrogenation zone effluent stream. It may also separate some or possibly all of the propylene into the light ends stream removed from this zone. The propylene may result from the dehydrogenation of propane present in the feedstream to the process or may be formed during the undesired cracking of butanes, which also produces the other light ends removed from this zone.

The particular dehydrogenation conditions employed within the reaction zone may vary depending on such factors as the catalyst activity, feed carbon number, and the desired conversion. The reaction zone conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 660° C., and the preferred operating pressure is about 0.5 to 2 atmospheres. The preferred butane dehydrogenation catalyst is comprised of a platinum group component, preferably platinum, a tin component and an alkali metal component with a porous inorganic carrier material. Other catalytic compositions may be used within this zone if desired. The preferred catalyst contains an alkali metal component chosen from cesium, rubidium, potassium, sodium, and lithium. The preferred alkali metal is normally chosen from lithium and potassium, with potassium being preferred for isobutane. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions are available in patents and other standard references.

The effluent from the dehydrogenation zone comprising isoolefins is passed to an etherification zone for reaction with an alcohol to produce the ether. The etherification reaction conditions are not narrowly critical and depend in large part upon the particular catalyst composition employed. Thus, both vapor phase and liquid phase processes have been proposed in which reaction temperatures are from about 50° C. to about 400° C., reaction pressures vary from about atmospheric to about 1.04 MPa (1500 psig) and stoichiometric molar ratios of alcohol to isoalkene range from 0.2:1 to about 10:1 and preferably, according to a near stoichiometric molar ratio ranging from about 0.95 to about 1.15. Thus, the present process may employ a near stoichiometric ratio of the alcohol with respect to the isoalkene. Both batch type and continuous process schemes may be suitably employed. In the present process the reaction can be carried out in either the vapor phase or the liquid phase, but the liquid phase is preferred. For reaction zone portions within distillation zones, the reaction proceeds primarily in the liquid phase. Isobutylene and isoamylene are the preferred isoalkenes. Methanol is the preferred alcohol, although ethanol may also be employed.

A wide variety of catalyst materials has been found to promote the etherification reaction including ion-exchange resins such as divinylbenzene cross-linked polystyrene ion exchange resins in which the active sites are sulfuric acid groups; and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of methanol or ethanol and isobutylene or isoamylene.

The reactor effluent stream from the etherification reaction zone comprises unreacted $C_4$–$C_6$ hydrocarbons and oxygenates. Generally, separation facilities are provided within a separation zone or the etherification zone for the bulk removal of oxygenate compounds. The effluent of the etherification reaction zone is passed into an intermediate point of a secondary fractionation column designed and operated to concentrate unconverted isoolefin and other saturated and unsaturated $C_4$–$C_6$ hydrocarbons present in the effluent into a net overhead stream. The net overhead stream of this column preferably is passed through a water wash zone to recover most of the methanol or other alcohol present in this stream. The bottoms stream of this column contains the product ether which is withdrawn as the product stream of the process. Further details on the separatory method and other aspects of the etherification zone may be obtained from the previously cited reference. Typically, the oxygenate depleted overhead stream is passed to a complete saturation zone. The remaining traces of oxygenate compounds are generally removed in a separate oxygenate removal unit as described in U.S. Pat. No. 5,245,107, hereby incorporated by reference. In the complete saturation zone, the oxygenate depleted net effluent stream is hydrogenated to fully saturate all of the olefinic hydrocarbons charged thereto while minimizing any cracking or polymerization of the hydrocarbons passing therethrough. U.S. Pat. No. 4,816,607 discloses the operation of this complete saturation zone and is hereby incorporated by reference.

The process of the present invention includes the modification of the separation zone of an etherification zone to replace the oxygenate removal step and the complete saturation process with a single-step process which selectively removes oxygenates and olefins as an extract stream and provides a treated stream comprising $C_4$–$C_6$ unreacted hydrocarbons. Thus, the process of the present invention may be employed to treat the $C_4$–$C_6$ feedstream in combination with the etherification zone unreacted effluent stream to remove impurities such as oxygenates, olefins, and sulfur compounds to provide an extract stream comprising the trace impurities and a treated stream comprising $C_4$–$C_6$ hydrocarbons. The treated stream is passed to an isomerization zone. The extract stream may be withdrawn for processing in an alkylation unit or treated for the removal of sulfur. A portion of the extract stream may be returned to the etherification zone for the further production of ether from the branched olefins.

DETAILED DESCRIPTION OF THE DRAWINGS

The process of the present invention is hereinafter described with reference to the Figures which illustrate various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the figures may be modified in many aspects without departing from the basic overall concept of the invention.

Figure 1:
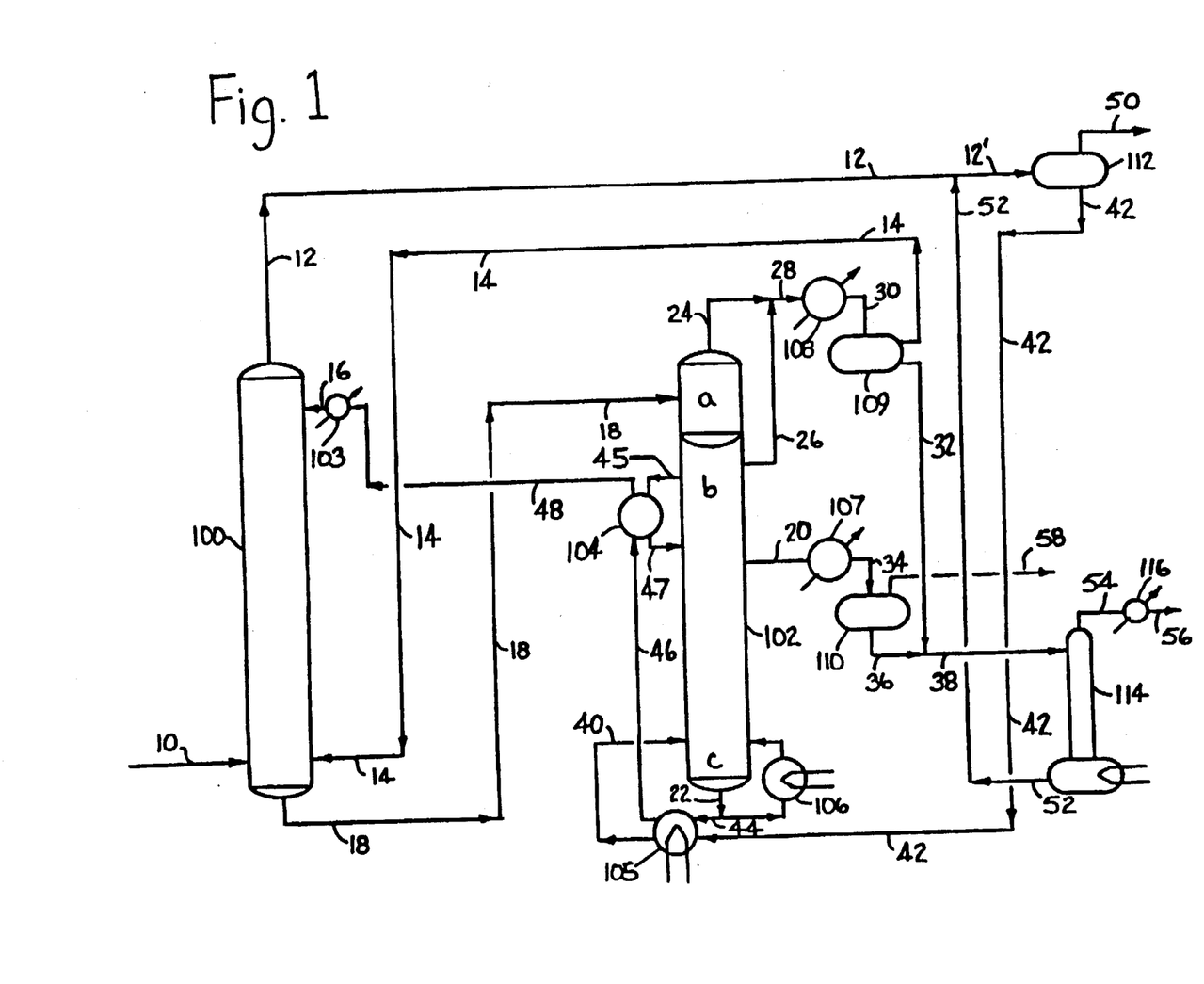
FIG. 1 is a schematic illustration of the process for the removal of sulfur compounds from a feedstream according to the process of the instant invention.

With reference to FIG. 1, a liquid feedstock comprising $C_4$–$C_6$ hydrocarbons with trace amounts of mercaptans, sulfides, olefins, and oxygenates is passed via line 10 to a liquid-liquid extraction zone 100. In this context, trace amounts of mercaptans means that the liquid feedstream contains between 1 and 5000 ppm wt mercaptans, 1 to 5000 ppm wt sulfides, and 1 to 5000 ppm wt oxygenates. The sulfides may include disulfides and thiosulfides. The oxygenates may include such components as alcohols, ethers, aldehydes, ketones and mixtures thereof. The olefins may include $C_3$ to $C_6$ mono- and di-olefins. In the liquid-liquid extraction zone 100, the feedstream 10 is contacted with a lean solvent in line 16 which has been chilled in cooler 103 to a temperature of between 0° C. and 200° C. and preferably cooled to a temperature between 0° C. and 100° C., and more preferably, cooled to a temperature between 0° C. and 50° C. A reflux stream 14 is introduced near the bottom of the extraction zone 100 to facilitate the separation of a rich solvent stream 18 which is withdrawn from the bottom of the extraction zone. A raffinate stream in line 12—having a reduced amount of mercaptans, sulfides, olefins, and oxygenates relative to the feedstream—is withdrawn from the top of the extraction zone and passed to a water-wash zone 112 via lines 12 and 12'. Preferably the raffinate is essentially free of mercaptans and sulfides and contains a reduced amount of oxygenates and olefins relative to the feedstream. A water stream is introduced to the raffinate stream in line 52 to remove any traces of the solvent which might have remained in stream 12', and the resulting mixture is separated in unit 112 into a product stream, or treated feedstream which is withdrawn in line 50 and a water phase which is removed in line 42. The treated feedstream 50 may be passed to an isomerization zone (not shown) for the isomerization of normal paraffins to isoparaffins. The rich solvent stream in line 18 is passed to an upper zone 102a of a stripping zone 102 wherein the rich solvent stream in line 18 is flashed to provide an overhead stream 24. The remaining liquid from the flash zone is contacted in zones b and c of the stripping zone with a stripping medium such as water or steam which is introduced in zone c of the stripping zone via line 40. The stripping zone inter heater 104 is typically operated by passing stream 45 withdrawn from zone b of the stripping column 102 in line 45 to provide a heated stream 47 which is returned to zone b of the stripping column 102. A bottoms stream is withdrawn from the stripping zone in line 22. A potion of the bottoms stream 22 is returned to stripping zone 102c as a reboiled fraction passing through reboiler 106, and the net bottoms stream is passed via line 44 to a stripper vaporizer 105 wherein heat from the net bottoms stream 44 is cross-exchanged with the stripping medium 42 to vaporize the stripping medium in line 40 and to provide a first cooled lean solvent stream in line 46. The first cooled lean solvent stream 46 is passed to an interheater 104 which provides heat to a portion of fluid within zone b of the stripping zone 102 and provides a second cooled lean solvent stream in line 48. The second cooled lean solvent stream 48 is passed to cooler 103 and returned to the extraction zone via line 16 as hereinabove described. A side draw stream is withdrawn from the stripping zone 102 via line 20 and passed to a side draw condenser 107 to provide a condensed side draw stream in line 34. The condensed side draw stream 34 comprises the concentrated impurities such as mercaptans, sulfides, olefins, oxygenates, water and mixtures thereof. The condensed side draw stream 34 is passed to accumulator 110 and a non-aqueous phase comprising the concentrated impurities is withdrawn in line 58 and a water stream is withdrawn in line 36. When the amount of trace impurities in the condensed side-draw stream 34 is sufficiently low enough to permit the trace impurities to be completely soluble in the water stream 36, there will be essentially no flow in stream 58, and the trace impurities will be recovered in streams 56 from a water still 114. When hydrocarbons such as olefins are present in line 34, the hydrocarbons are separated in accumulator 110 and withdrawn in line 58. The hydrocarbons withdrawn in line 58 may be sold or used for further processing. The overhead stream 24 from zone a of stripping zone 102 is combined with a vapor stream 26 withdrawn from zone b of the stripping column 102, and the vapor admixture is passed via line 28 to overhead condenser 108 to provide a cooled overhead stream 30. The cooled overhead stream 30 is passed to accumulator 109. In accumulator 109 a hydrocarbon phase and an aqueous phase are formed and the hydrocarbon phase is passed via line 14 as a reflux stream to the extraction zone 100. The aqueous phase is passed via line 32 to be admixed with the water stream line 36, and the water admixture is passed via line 38 to a water still 114. The water still 114 is reboiled with available medium or low pressure steam to provide a rejected stream 54 comprising the sulfur compounds and oxygenates. The rejected stream 54 is passed to condenser 116 wherein the rejected stream is cooled to provide a condensed stream in line 56. The condensed stream 56 comprising mercaptan sulfur may be collected and passed to a refinery sour water stripper for further disposal. When the mount of olefin in the feedstream is significant, a portion of the extract stream 58 comprising oxygenates and sulfur compounds may be passed to an etherification zone for the production of ethers. The sulfur compounds and the oxygenate compounds will generally not adversely affect the reaction of the olefins in the etherification zone and a portion of these sulfur compounds and oxygenates will be removed in the aqueous phase. A water stream, depleted in sulfur and oxygenates, is passed via line 52 to provide a wash water stream for the raffinate in line 12.

In the above described scheme, the liquid-liquid extraction zone is operated as a liquid-liquid extractor wherein the feedstream is introduced as a liquid hydrocarbon stream. In this operation, the liquid-liquid extraction column 100 typically is operated at conditions to maintain all of the streams in liquid state. Such operations would include a pressure ranging from approximately 50 kPa to approximately 7 MPa and a temperature ranging from about 0° C. to approximately 200° C. The solvent regeneration operation of the stripping zone 102 may be characterized by regeneration operating conditions including a pressure ranging from about 50 kPa to approximately 3.5 MPa and a temperature ranging from approximately 100° C. to approximately 400° C. The water still 114, when required, is conventionally operated at temperatures ranging from 20° C. to approximately 150° C. and a pressure ranging from 50 kPa to approximately 500 kPa.

Figure 2:
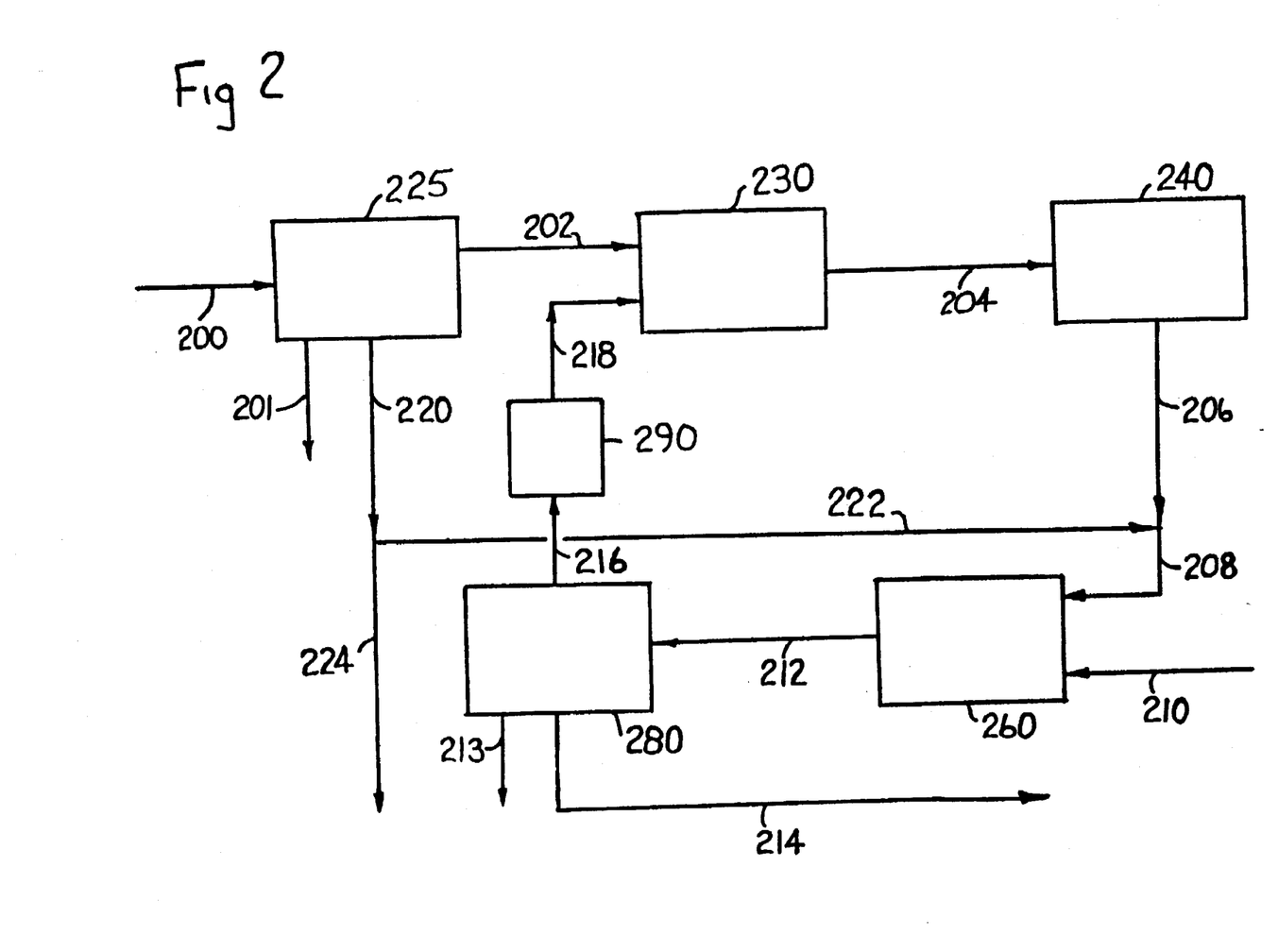
FIG. 2 is a schematic process flow scheme for the production of ethers according to the process of the present invention.

With reference to FIG. 2, a feedstream comprising $C_4$–$C_6$ hydrocarbons with mounts of at least one of sulfur compounds such as mercaptans and sulfides, olefins, and oxygenates is passed via line 200 to an extraction zone 225 of the present invention as described in FIG. 1 herein above. In this context, amounts of mercaptans means that the liquid feedstream contains between 1 and 5000 ppm/wt mercaptans, 1 to 5000 ppm/wt sulfides, and 1 to 5000 ppm/wt oxygenates. The oxygenates may include such components as alcohols, ethers, aldehydes, ketones, and mixtures thereof. Water may also present. A raffinate stream in line 202—following a water wash step and being essentially free of mercaptans, sulfides, and oxygenates and having a reduced amount of olefins relative to the feedstream and saturated with water—is withdrawn from the extraction zone and passed to an isomerization zone 230. A small stream 201 comprising water soluble impurities is withdrawn from zone 225 in line 201 and sent to further treating for proper disposal. An extract stream 220, enriched in impurities such as sulfur compounds and olefins is withdrawn from the extraction zone 225. At least a portion of line 220 is passed to an etherification zone 260. A portion of the extract stream 224 may be withdrawn as a feed to an alkylation unit for the production of motor gasoline. In the isomerization zone, the isoparaffins are selectively isomerized to provide an isomerized paraffin stream 204. The isomerized paraffin stream 204 is passed to a dehydrogenation zone 240, wherein the isoparaffins are converted to iso-olefins and a dehydrogenation zone effluent comprising isoolefins is withdrawn in line 206. The dehydrogenation effluent, or isoolefin stream 206 is preferably combined with at least a portion of the extract stream 222 and passed to an etherification zone 260 via line 208. In the etherification zone 260, a monohydroxyl alcohol in line 210 such as methanol or ethanol is reacted with the isoparaffins over an etherification catalyst to produce an etherification effluent, which is withdrawn via line 212. The etherification effluent 212 is passed to a separation zone 280 wherein the ether product 214 is separated by fractionation from unreacted $C_4$–$C_6$ hydrocarbons which are withdrawn in line 216. It is conventional to locate a portion of the etherification zone 260 within the separation zone 280 by employing a technology known as catalytic distillation as exemplified in U.S. Pat. No. 5,348,707, hereby incorporated by reference. Any oxygenates and sulfur compounds present in the extract stream 222 portion will not adversely affect the etherification reaction, but must be removed prior to returning unreacted $C_4$–$C_6$ hydrocarbons to the isomerization zone 230 where such impurities would harm the catalyst. Unreacted olefins in the extract stream 222 also must be removed from the unreacted $C_4$–$C_6$ hydrocarbons. Typically, in the separation zone 280 the unreacted $C_4$–$C_6$ hydrocarbons are treated first for the bulk removal of the alcohol in a water wash to provide an unreacted $C_4$–$C_6$ hydrocarbon stream comprising trace oxygenates. The trace oxygenates are passed to an oxygenate removal zone (not shown) such as a process as described in U.S. Pat. No. 5,245,107, and an oxygenate-free stream is passed in line 216 to a complete saturation zone 290. In the complete saturation zone 290, unreacted linear-olefins and diolefins are saturated over a noble metal catalyst in the presence of hydrogen to provide a recycle stream 218 comprising untreated $C_4$–$C_6$ hydrocarbons which is returned to the isomerization zone 230. When the feedstream 200 comprises sulfur and olefin compounds, the sulfur compounds such as mercaptans are rejected in the extract stream 220, which will also comprise olefins. A portion of the extract stream 220 may be withdrawn in line 224 and passed to a mercaptan removal zone and an alkylation zone (not shown) for the conversion of the olefins to alkylate, or a portion of the extract stream 220 may be passed to the etherification zone 260 as described hereinabove. Any sulfur present in stream 220 will be rejected in a light ends stream 213 withdrawn from the separation zone 280 or in the ether product stream 214.

Figure 3:
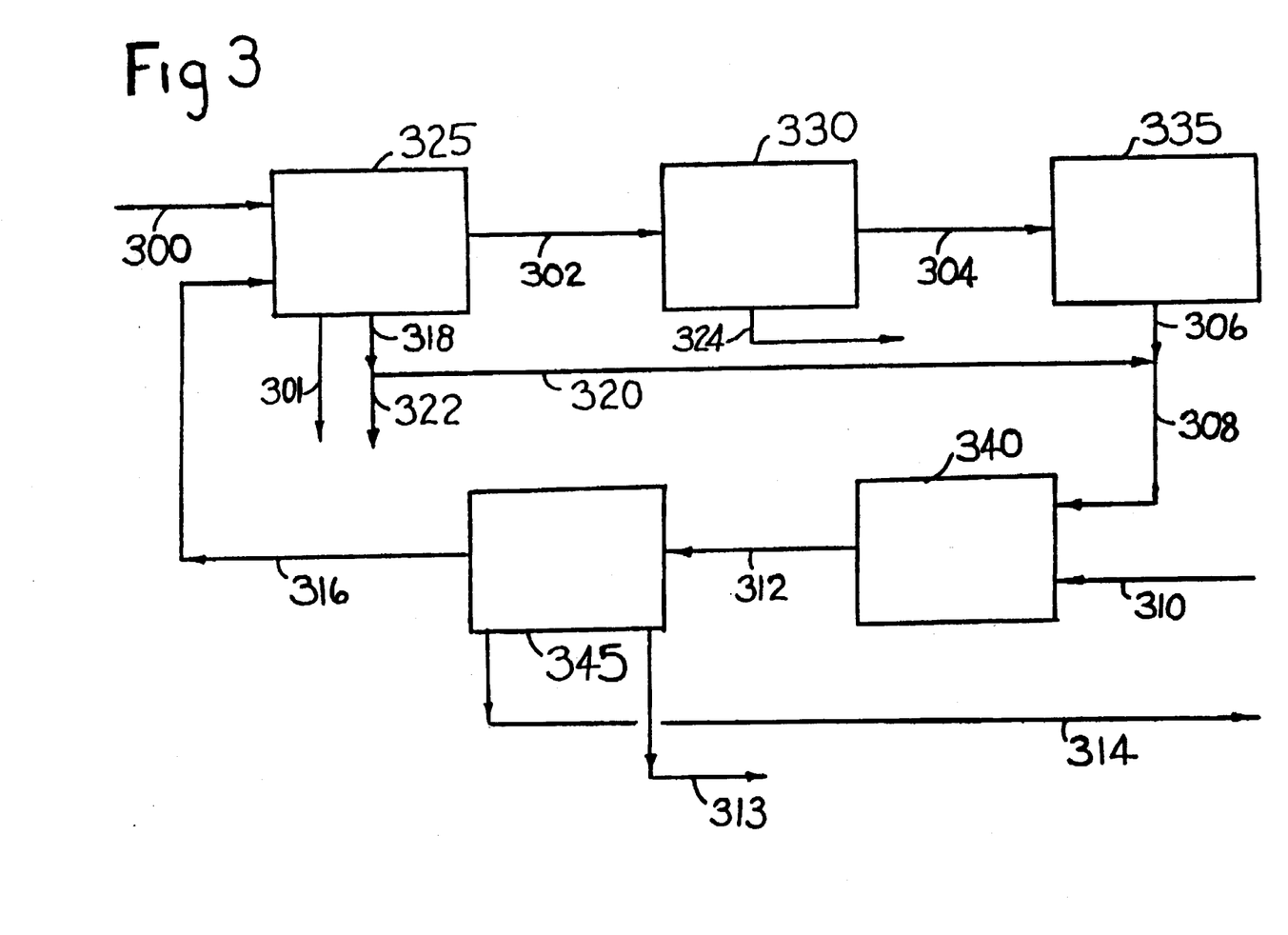
FIG. 3 is a schematic process flow scheme for the production of ethers according to the present invention processing both the feedstream and the recycle stream.

With reference to FIG. 3, the feedstream 300 comprising $C_4$–$C_6$ hydrocarbons with trace impurities including sulfur compounds, oxygenates, and olefins is combined with a recycle stream 316 comprising unreacted $C_4$–$C_6$ hydrocarbons to provide a feed admixture and the feed admixture is passed to an extraction zone 325. In the extraction zone 325, as described in FIG. 1, the feed admixture is contacted with a selective solvent to provide a raffinate stream essentially free of impurities in line 302 and an extract stream enriched in the impurities is withdrawn in line 318. The water soluble components of the feedstream removed by the extraction zone 325 are withdrawn as a waste water stream in line 301. The waste water stream may be sent to a waste water disposal unit for further treating. The extract stream 318 will contain hydrocarbons such as olefins extracted from the feedstream and any sulfur compounds which are not soluble in the aqueous phase. The portion of the extract stream 318 may be passed in line 322 to a downstream processing unit such as an alkylation unit for conversion of the olefins to alkylate. A portion of the extract stream 318 may be passed in line 320 and 308 to the etherification zone 340 to minimize loss of olefins. Any sulfur compounds passed to the etherification zone 340 will either be rejected with light ends stream 313 or be removed with the heavy ether product in line 314. To prevent the buildup of linear olefins in the etherification zone, the portion of the extract removed in line 322 should range from about 1 to about 10 percent of the total extract stream flow. The raffinate stream 302 is passed to an isomerization zone 330 wherein normal paraffins are isomerized to provide an isomerization effluent stream 304. In the associated fractionation of the isoparaffins, a stream comprising heavy compounds is rejected in line 324. These rejected compounds may be blended into motor gasoline. The rejected heavy compounds in line 324 include $C_6^+$ hydrocarbons, heavy oxygenates and mixtures thereof. The isomerization effluent 304 is passed to a dehydrogenation zone 335 wherein the isoparaffins are dehydrogenated to provide a dehydrogenation effluent 306 comprising isoolefins. The dehydrogenation effluent, or isoolefin stream, 306 is admixed with at least a portion of the extract stream in lines 318 and 320 to provide an etherification feed in line 308. The etherification feed 300 is combined with about a stoichiometric amount of monohydroxyl alcohol 310 such as methanol or ethanol over an etherification catalyst to provide an etherification effluent 312. The etherification effluent 312 is passed to a separation zone 345 to provide an ether product 314 and an unreacted $C_4$–$C_6$ hydrocarbon stream 316. As described herein above with respect to FIG. 2, a portion of the etherification reaction is preferably carried out in the separation zone 345 by a technique known as catalytic distillation. In the separation zone 345, the etherification effluent 312 is stripped to reject light ends and oxygenates in line 313 which may be directed to fuel. At least a portion of the unreacted $C_4$–$C_6$ hydrocarbon stream is returned to the extraction zone 325 as the recycle stream 316.

The use of the extraction zone 325 in this service eliminates the need for the complete saturation zone 290 of FIG. 2 to remove olefins and results in a more simplified overall flow scheme for the production of ethers. Furthermore, by the elimination of the complete saturation zone, the process scheme becomes less sensitive to changes in feedstock quality by the ability to reject impurities before they are introduced to sensitive processing areas. Processing schemes with fewer processing steps reduce the complexity of the overall production and reduce the capital cost by eliminating separate serial treating steps. The ability to process lower quality feeds provides an increased processing flexibility and economic advantage because more contaminated feedstocks have a lower value. The concentration of both sulfur and oxygenates in a single, small stream provides a further processing opportunity. Because the extract stream typically ranges from 1 to 20 volume percent of the original feedstream, subsequent treatment for removal of sulfur compounds can be accomplished economically by catalytic hydrotreating or extraction prior to recovery, conversion, or use as fuel. The extract stream comprising sulfur and olefins may be further processed to remove a portion of both sulfur and olefins in a process for thio-etherification of olefins as disclosed in U.S. Pat. No. 4,175,467. Accordingly, the extract is passed to a thio-etherification zone to combine the sulfur and olefins to form a thio-ether and upon subsequent fractionation to remove the heavier thio-ether, a second treated stream essentially free of sulfur and olefins is produced. The advantages of the combined extraction and thioetherification zones are reduced operating cost of the extraction zone combined with the resulting lower cost of separating the remaining sulfur and olefins from the extract stream.

The invention will be more fully understood by reference to the following examples, and comparative data which demonstrate the high selectivity of the process and the solvents for the removal of trace impurities from the hydrocarbon feedstream.

EXAMPLES

Example I

An engineering simulation of process of the present invention, as depicted in FIG. 1, for rejecting sulfur compounds from a $C_4$ hydrocarbon feedstream to an isomerization zone was evaluated. As shown in Table 1, the hydrocarbon feedstream contained about 370 ppm-wt of impurities and about 300 ppm-wt water to be removed.

TABLE 1

| Component | FEED PPM-WT | PRODUCT PPM- |
|---|---|---|
| methyl mercaptan | 60 | — |
| Ethyl mercaptan | 150 | 7 |
| diMethyl Sulfide | 100 | 4 |
| Methanol | 50 | — |
| Isopropyl Alcohol | 10 | — |
| TOTAL IMPURITIES | 370 | 11 |
| Water | 300 | 160 |
| TOTAL WATER IMPURITIES | 670 | 171 |

The hydrocarbon feedstream also contained about 94.3 wt % normal butane, 2.3 wt % isobutane, 3.0 wt % normal pentane and 0.4 wt % 2-butene.

The feedstream was passed to the liquid-liquid extraction at a temperature of about 37° C. wherein the feedstream was contacted with a solvent stream introduced near the top of the extractor at a temperature of about 49° C. The extractor was maintained at a temperature of about 49° C. and a pressure of about 690 kPa. A reflux stream was introduced at a bottom of the extractor at a temperature of about 26° C. A rich solvent stream consisting of tetraethylene glycol was passed to a stripping column operating at a temperature of about 166° C. and a pressure of about 310 kPa. Stripping water was introduced to the stripping column at a temperature of about 109° C.

The results of the simulation indicated in Table 1 show that essentially all of the sulfur compounds are removed by the process of the present invention. The level of sulfur impurities was reduced from about 310 ppm wt to about 11 ppm wt, a reduction of over 96 percent. The level of oxygenates was also reduced from about 60 ppm wt to an undetectable amount. Furthermore, the water level was reduced from about 300 ppm wt to about 160 ppm wt, a 46% reduction. The raffinate withdrawn from the extractor comprising the treated feedstream, depleted in sulfur compounds represented about 96% of the feedstream charged to the extractor. Thus, the sulfur compounds and other impurities were concentrated into the extract, a stream less than 4 wt % of the original feedstream. The extract stream comprising the impurities may be used as fuel or treated further to remove the impurities. If treated further in a mercaptan extraction process, the capacity of the mercaptan extraction process relative to the original feedstream will be significantly smaller and less costly than one required to treat the entire feedstream.

Example II

The process as shown in FIG. 1 was further studied by engineering simulation for a variety of selective solvents for the $C_4$ hydrocarbon feedstream of Example I. Table 2 shows the effectiveness of the solvents for removal of sulfur compounds and oxygenates while rejecting a minimum amount of an extract stream comprising these impurities. Raffinate recoveries of treated feedstream ranged from 99.5 to 99.9 wt % based on the total weight of the feedstream. The glycerol solvent required the rejection of about 0.5 wt % of the feedstream, but was unable to reduce ethyl mercaptan below about 69 ppm wt. The use of the other solvents with the rejection of about 0.2 wt % or less resulted in treated feedstreams with less than about 16 ppm-wt sulfur compounds and less than about 2 ppm wt oxygenates.

TABLE 2

SIMULTANEOUS REMOVAL OF SULFUR COMPOUNDS AND OXYGENATES FROM BUTANE

| | OXYGEN/SULFUR SELECTIVE SOLVENTS | | | | |
|---|---|---|---|---|---|
| | GROL | DEG | TEG | TETRA | SULF |
| $C_4$ FEEDSTREAM (1 lb/hr) | 1000.0 | 1000.0 | 1000.0 | 1000.0 | 1000.0 |
| RAFFINATE (1 lb/hr) | 995.1 | 998.4 | 997.9 | 999.3 | 999.3 |
| EXTRACT (1 lb/hr) | 4.9 | 1.6 | 2.1 | 0.7 | 0.7 |
| EXTRACT (wt. %) | 0.5% | 0.2% | 0.2% | 0.1% | 0.1% |
| SOLVENT/FEED (vol/wt) | 0.82/1.8 | 0.84/1.7 | 0.91/1.8 | 1.04/1.8 | 0.92/2.0 |
| % RECOVERIES OF | | | | | |
| Methyl Mercaptan | 99.77 | 100.0 | 100.0 | 100.0 | 100.0 |
| Ethyl Mercaptan | 53.96 | 95.85 | 97.38 | 98.49 | 95.32 |
| Methyl Sulfide | 96.55 | 90.21 | 95.14 | 94.93 | 95.45 |
| Methyl Alcohol | 99.71 | 99.79 | 99.96 | 99.98 | 99.96 |
| Isopropyl Alcohol | 99.99 | 99.94 | 99.87 | 99.84 | 88.58 |
| ppm in N—$C_4$ Pdt | | | | | |
| Methyl Mercaptan | <1 | <1 | <1 | <1 | <1 |
| Ethyl Mercaptan | 69.4 | 6.1 | 3.9 | 2.3 | 7.0 |
| Methyl Sulfide | 3.5 | 9.6 | 4.9 | 5.1 | 4.5 |
| Methyl Alcohol | <1 | <1 | <1 | <1 | <1 |
| Isopropyl Alcohol | <1 | <1 | <1 | <1 | 1.1 |

GROL = Glycerol; DEG = Diethylene glycol; TEG = Triethylene glycol; TETRA = Tetraethylene glycol; SULF = Sulfolane

Example III

In order to measure the selectivity of the solvent for absorbing olefins as used in the process of the present invention, a 1000 ml sample of each of butane, 2-butene, and mercaptan was prepared and the relative volatility of each of the components was measured at 40° C. with and without the selective solvent. The results shown in Table 3 for a mixture of butane and 2-butene alone and in a 1 mol-% solution with tetraethylene glycol clearly show that the solvent increases the relative volatility of the two components from 1.08 to 1.93. This observed 2 fold increase in relative volatility suggests that the use of solvent extraction or absorption will result in the separation of the $C_4$ olefins from the $C_4$ paraffins in the process of the present invention.

Example IV

As in Example III, the effect of the solvent on the relative volatility between butane and methyl mercaptan was measured in a 1000 ml sample. The results shown in Table 3 indicate that relative volatility of the ratio of the butane to the mercaptan increased about 10 times in the tetraethylene glycol (TETRA) solvent at a level of 1 mol-% in the solvent. This increase suggests a strong tendency for the separation of the mercaptan from the $C_4$ paraffin in the solvent-based absorption and extraction process of the current invention.

TABLE 3

RELATIVE VOLATILITY @ 40° C.

|  | NO SOLVENT | WITH TETRA |
|---|---|---|
| BUTANE/BUTENE | 1.08 | 1.93 |
| BUTANE/MERCAPTAN | 1.2 | 12 |

Example V

The relative volatility between butane and 2-butene, a representative iso-olefin, was evaluated according to the procedure of Example IV with 0.5 mole % TETRA solvent added to a binary mixture of n-butane and 2-butene. Table 4 presents the relative volatility of n-butane over 2-butene at 40°, 80°, and 120° C. These results showed that the relative volatility can be improved from about 65 to about 100 percent by the addition of tetraethylene glycol.

TABLE 4

VAPOR PRESSURE RATIO OF N-BUTANE/2 BUTENE

| TEMPERATURE, °C. | NO SOLVENT | WITH TETRA |
|---|---|---|
| 40 | 1.02 | 2.03 |
| 80 | 1.00 | 1.65 |
| 120 | 0.98 | 1.57 |

Example VI

An engineering simulation of a conventional etherification complex as described in U.S. Pat. No. 4,816,607 for the production of MTBE was developed for a feedstream comprising isobutane and normal butane with the following composition:

| COMPONENT | Wt-% |
|---|---|
| propane | 1.8 |
| i-Butane | 28.3 |
| n-Butane | 68.9 |
| i-Pentane | 1.0 |

The feedstream was treated in the conventional manner to reduce contaminants to less than the following levels:

| Contaminant: | ppm-wt |
|---|---|
| Sulfur | 10 |
| Oxygenates | 10 |
| Olefins | 1000 |
| Water | 10 |

The results of a material balance on the complex are shown in Table 5 as the Base Case, producing about 600,000 metric tonnes per annum. The base case scheme employed an oxygenate removal unit to remove residual oxygenates from the unreacted hydrocarbons withdrawn from the etherification zone and a complete saturation unit to convert any olefins to paraffins prior to returning the unreacted hydrocarbons to the isomerization zone.

TABLE 5

SUMMARY OF MTBE SCHEMES (ALL FLOWS IN KG/HR)

|  | BASE CASE | SCHEME A | SCHEME B |
|---|---|---|---|
| CAPACITY: |  |  |  |
| Extraction Zone | — | 60 | 124 |
| Isomerization Zone | 76 | 73 | 73 |
| Dehydrogenation Zone | 124 | 115 | 115 |
| Etherification Zone | 120 | 115 | 113 |
| Oxygenate Removal | 64 | — | — |
| Complete Saturation Zone | 64 | — | — |
| FEEDS: |  |  |  |
| Field Butane | 62 | 62 | 65 |
| Alcohol | 30 | 28 | 28 |
| PRODUCTS: |  |  |  |
| MTBE | 83 | 78 | 78 |
| Net Extract | — | 4 | 8 |

Example VII

The conventional etherification scheme was modified as shown in FIG. 2 and evaluated by engineering simulation for the same feed and feed rate of Example VI. The results of this evaluation are shown in Table 5 as Scheme A. The substitution of the extraction zone of the present invention for the oxygenate removal unit and the complete saturation zone resulted in the production of about 4 kg/hr of an extract stream comprising about 50 mol-% olefins and having about the following contaminants:

| Oxygenates | 1,000 ppm-wt |
|---|---|
| Water | 600 ppm-wt |

Example VIII

A scheme for the production of MTBE from an untreated feedstream according to the process flow described in FIG. 3 was developed as Scheme B. In Scheme B, the untreated feedstream contained the same amount of butanes as that of Example VI with the following additional components:

| Sulfur |  |
|---|---|
| Mercaptan, ppm-wt | 400 |
| Dimethylsulfide, ppm-wt | 40 |
| Oxygenates, ppw-wt | 1000 |
| Olefins, wt-% | 5 |

Accordingly, the rate of the feedstream was increased to 65 kg/hr to provide the same amount of paraffins to the complex which produced the same amount of MTBE as Scheme A. The results of the simulation are shown as Scheme B in Table 5. In Scheme B, the extract was produced at a rate of about 8 kg/hr and had the following composition:

| Olefins, mol-% | 50 |
|---|---|
| Sulfur |  |
| Mercaptans, ppm-wt | 3000 |
| Di-Methyl sulfide, ppm-wt | 300 |

| Oxygenates | |
|---|---|
| Di-methyl Ether, ppm-wt | 4500 |
| Methanol, ppm-wt | 400 |
| MTBE, ppm-wt | 2000 |
| water, ppm-wt | 300 |

Thus, Scheme B without the oxygenate removal unit, the complete saturation unit, or the feedstream pretreatment zone significantly simplified the processing steps for the production of MTBE and permitted the single-step processing of lower quality feeds with high olefin, sulfur, and oxygenate contaminant levels which are generally unacceptable for etherification complexes.

We claim:

1. A process for the removal of impurities comprising at least one of sulfur compounds, oxygenates, and olefins from a $C_4$–$C_6$ hydrocarbon feedstream comprising said impurities, said process comprising:

a) passing said feedstream to a removal zone and therein contacting said feedstream with a lean selective solvent selected from the group consisting of diethylene glycol, triethylene glycol, tetraethylene glycol, pentaethylene glycol, 1,3-butane glycol, 1,2-butane glycol, 1,5-pentane glycol, sulfolane, furfural, n-formyl morpholine, n-methyl-2 pyrrolidone, water, and mixtures thereof to provide a treated feedstream depleted in said impurities relative to said feedstream and a rich solvent stream;

b) passing said rich-solvent stream to a stripping zone and therein contacting said rich solvent stream with a stripping medium to provide an extract stream enriched in said impurities relative to said feedstream and a regenerated selective solvent stream;

c) renaming at least a portion of said regenerated selective solvent stream to said removal zone as said lean selective-solvent.

2. The process of claim 1 wherein said removal zone is a liquid-liquid extraction zone and said feedstream is a liquid feedstream.

3. The process of claim 1 wherein said removal zone is an absorption zone and said feedstream is a vapor feedstream.

4. The process of claim 1 further comprising passing the treated feedstream to an isomerization zone.

5. The process of claim 1 further comprising passing at least a portion of said extract stream to an alkylation zone to produce an alkylate.

6. A process for the removal of impurities including at least one of sulfur compounds, oxygenates and olefins from a liquid feedstream comprising a mixture of said impurities and $C_4$ and $C_6$ hydrocarbons said process comprising:

a) passing said liquid feedstream and a reflux stream at extraction conditions including an extraction temperature and an extraction pressure to a liquid-liquid extraction zone and therein contacting said feedstream and said reflux stream with a selective solvent stream to provide a treated feedstream depleted in said impurities and a rich-solvent stream, enriched in said impurities relative to the selective solvent stream;

b) passing at least a portion of the rich-solvent stream at solvent regeneration conditions including a regeneration temperature and a regeneration pressure to a stripping zone and therein contacting said rich-solvent stream with a stripping medium stream to provide a reflux stream, an extract stream, and a lean-solvent stream; and, c) passing at least a portion of the lean-solvent stream to the extraction zone to provide said selective solvent stream.

7. The process of claim 6 wherein the selective solvent is selected from the group consisting of diethylene glycol, triethylene glycol, tetraethylene glycol, pentaethylene glycol, 1,3-butane glycol, 1,2-butane glycol, 1,5 pentane glycol, and mixtures thereof.

8. The process of claim 6 wherein the selective solvent is selected from the group consisting of sulfolane, furfural, n-formyl morpholine, and n-methyl-2 pyrrolidone.

9. The process of claim 6 wherein said extraction temperature ranges from about 0° C. to about 200° C. and said extraction pressure ranges from about 50 kPa to about 7 MPa.

10. The process of claim 6 wherein said regeneration temperature ranges from about 100° C. to about 400° C. and said regeneration pressure ranges from about 50 kPa to about 3.5 MPa.

11. A process for the removal of impurities including at least one of sulfur compounds, oxygenates and olefins from a vapor feedstream comprising a mixture of said impurities and $C_4$–$C_6$ hydrocarbons said process comprising:

a) passing said vapor feedstream at absorption conditions to an absorption zone and therein contacting said feedstream with a selective solvent stream to provide a treated feedstream depleted in said impurities and a rich-solvent stream, enriched in said impurities relative to the selective solvent stream;

b) passing at least a portion of the rich-solvent stream at solvent regeneration conditions including a regeneration temperature and regeneration pressure to a stripping zone and therein contacting said rich-solvent stream with a stripping medium stream to provide a reflux stream, an extract stream, and a lean-solvent stream; and c) passing at least a portion of the lean-solvent stream to the absorption column to provide said selective solvent stream.

12. The process of claim 11 wherein the selective solvent comprises a polyalkylene glycol of the formula:

wherein n is a integer from 1 to 5, m is an integer from 1 to 8, and $R_1$, $R_2$, and $R_3$ may each be hydrogen, alkyl, aryl, aralkyl, alkylaryl, and mixtures thereof and having a molecular weight less than about 400.

13. The process of claim 12 wherein the sulfur selective solvent further comprises a glycol ether cosolvent of the formula:

wherein $R_4$, $R_5$, $R_6$ and $R_7$ may each be hydrogen, alkyl, aryl, aralkyl, alkylaryl, and mixtures thereof with the proviso that $R_4$ and $R_7$ are not both hydrogen; x is an integer from 1 to 5; and y may be an integer from 2 to 8 and said solvent comprises between 0.5 and 99 percent by weight of said glycol ether cosolvent.

* * * * *

UNITED STATES PATENT AND TRADEMARK OFFICE
CERTIFICATE OF CORRECTION

PATENT NO. : 5,689,033
DATED : Nov. 18, 1997
INVENTOR(S) : PAULINO FORTE and STANLEY J. FREY It is certified that error appears in the above-identified patent and that said Letters Patent is hereby corrected as shown below:

Claim 1 should read as follows:

1. A process for the removal of impurities comprising at least one of sulfur compounds, oxygenates, and olefins from a $C_4$-$C_6$ hydrocarbon feedstream comprising said impurities, said process comprising:

a) passing said feedstream to a removal zone and therein contacting said feedstream with a lean selective solvent selected from the group consisting of diethylene glycol, triethylene glycol, tetraethylene glycol, pentaethylene glycol, 1,3-butane glycol, 1,2-butane glycol, 1,5-pentane glycol, sulfolane, furfural, n-formyl morpholine, n-methyl-2 pyrrolidone, water, and mixtures thereof to provide a treated feedstream depleted in said impurities relative to said feedstream and a rich solvent stream;

b) passing said rich-solvent stream to a stripping zone and therein contacting said rich solvent stream with a stripping medium to provide an extract stream enriched in said impurities relative to said feedstream and a regenerated selective solvent stream;

UNITED STATES PATENT AND TRADEMARK OFFICE
CERTIFICATE OF CORRECTION

PATENT NO. : 5,689,033
DATED : Nov. 18, 1997
INVENTOR(S) : PAULINO FORTE and STANLEY J. FREY It is certified that error appears in the above-identified patent and that said Letters Patent is hereby corrected as shown below:

c)  [renaming] returning at least a portion of said regenerated selective solvent stream to said removal zone as said lean selective-solvent.

Signed and Sealed this

Twentieth Day of January, 1998

Attest:

BRUCE LEHMAN

Attesting Officer

Commissioner of Patents and Trademarks